United States Patent
Wadstrom et al.

(10) Patent No.: US 6,599,504 B1
(45) Date of Patent: Jul. 29, 2003

(54) **STRAIN OF BACTERIA OF THE SPECIES *LACTOBACILLUS PARACASEI* SUBSP. *PARACASEI*, COMPOSITION THEREOF FOR USE IN FOOD AND PRODUCT CONTAINING SAID STRAIN**

(75) Inventors: Torkel Wadstrom, Lund (SE); Per Aleljung, Lund (SE); Ulla Svensson, Lund (SE); Rangne Fonden, Stockholm (SE)

(73) Assignee: Arla Ekonomisk Forening, Stockholm (SE)

( * ) Notice: Subject to any disclaimer, the term of this patent is extended or adjusted under 35 U.S.C. 154(b) by 0 days.

(21) Appl. No.: 09/555,954

(22) PCT Filed: Dec. 8, 1998

(86) PCT No.: PCT/SE99/02263
§ 371 (c)(1),
(2), (4) Date: Sep. 22, 2000

(87) PCT Pub. No.: WO99/29833
PCT Pub. Date: Jun. 17, 1999

(30) Foreign Application Priority Data

Dec. 8, 1997 (SE) ................................ 9704577

(51) Int. Cl.$^7$ ............................ A01N 63/00; C12N 1/20
(52) U.S. Cl. ................................ 424/93.45; 435/252.9; 424/439
(58) Field of Search ................ 424/93.45, 439; 435/252.9

(56) References Cited

U.S. PATENT DOCUMENTS 5,716,615 A * 2/1998 Cavaliere Vesely ........ 424/93.4

FOREIGN PATENT DOCUMENTS

WO    WO 97/09448    3/1997

OTHER PUBLICATIONS

Dellaglio, et al., "Designation of ATCC 334 in Place of ATCC 393 (NCDO 161) as the Neotype Strain of *Lactobacillus casei* subsp. *casei* and Rejection of the Name *Lactobacillus paracasei* (Collins et al., 1989)", International Journal of Systematic Bacteriology, Apr. 1991, p. 340–342.

Mercenier et al., "Development of lactic acid bacteria as live vectors for oral or local vaccines", Dialog Information Services, Biosis Review, Dialog Accession No. 1333687, Biosis No. 99333687, Advances in Food Sciences 18 (3–4), 1996.

Harty et al., "Pathogenic potential of lactobacilli", Dialog Information Services, Biosis Review, Dialog Accession No. 11493893, Biosis No. 98093893, International Journal of Food Microbiology 24(1–2), 1994.

Guenter et al., "Total soluble cytoplasmatic protein patterns of *Lactobacillus rhamnosus* and Lactobacillus . . . ", Chemical Abstracts, vol. 125, No. 23, Dec. 2, 1996.

Savova et al., "*Lactobacillus casei*: Survival in the gastrointestinal tract and biostimulating activity", Dialog Information Services, Biosis, Dialog Accession No. 11400418, Biosis No. 199800181750, Zhivotnowdni Nauki 33 (7–8), pp. 55–57, 1996.

Gilliland et al., "De conjugation of bile acids by intestinal lactobacilli", Dialog Information Services, Biosis, Dialog Accession No. 02137076, Biosis No. 000063052076, Appln. Environ. Microbiol 33 (1), 1977, 15–18.

ATCC Catalogue of Bacteria, 1996, p. 193.*

Klein et al., Mikoekol. Ther., 1995, 23, p. 179–187.*

* cited by examiner

*Primary Examiner*—Irene Marx
(74) *Attorney, Agent, or Firm*—Larson & Taylor PLC

(57) ABSTRACT

Strain of Lactobacillus useful as probiotics in food and naturopathic medicines and which is resistant in vitro against hydrochloric acid and gastric juices and tolerates bile salts without deconjugating them whereas strong assimilation is occurring and which has good survival at the passage through the stomach and the gastrointestinal tract and which strain is growing optimally at about 37° C., which strain is *Lactobacillus paracasei* subsp. *paracasei*, which is a Gram-positive, homofermentative, rod-shaped bacterium capable of producing L-lactic acid and containing three plasmids having a size of 2.2, 4.36 and 9.1 Kb, respectively. The invention also relates to a composition containing the strain and a product consisting of or containing a concentrate of the strain.

24 Claims, No Drawings

STRAIN OF BACTERIA OF THE SPECIES *LACTOBACILLUS PARACASEI* SUBSP. *PARACASEI*, COMPOSITION THEREOF FOR USE IN FOOD AND PRODUCT CONTAINING SAID STRAIN

This application was filed under 35 USC 371 as the national phase of PCT/SE98/02263 filed Dec. 8, 1998.

The present invention relates to a strain of *Lactobacillus paracasei* subsp. *paracasei*, a composition thereof for use in food as well as a product containing said strain.

Definition and Characterisation of the Strain

The novel strain (which in the following for simplicity will be designated LMG-P-17806) is a variant of the species *Lactobacillus paracasei* subsp. *paracasei*. It has the characteristics of the species with a GC-content of 44%. LMG P-17806 has been isolated from samples from the gastrointestinal micro-flora of humans. LMG-P-17806 is a Gram-positive, homofermentative rod-shaped bacteria. It produces L-lactic acid (laevorotatory stereoisomer of lactic acid) and grows optimally at 37° C. The stain is characterized by being tolerant in-vitro against hydrochloric acid and gastric juice by tolerating bile salts without deconjugating them and by having a great ability of assimilating cholesterol. The stain is also characterized by containing three plasmids having a size of 2.2, 4.36 and 9.1 Kb, respectively. Other characteristics are that the strain is fermenting ribose, adonitol, galactose, glucose, fructose, mannose, sorbose, mannitol, sorbitol, N-acetyl-glucosamine, esculin, cellobiose, maltose, lactose, sucrose, trehalose, inulin, melezitose, D-turanose and D-tagatose. On the other hand it does not ferment glycerol, erythritol, D- and L-arabinose, D- and L-xylose, β-methyl-D-xyloside, rhamnose, dulcitol, inositol, α-methyl-D-mannoside, α-methyl-D-glucoside, amygdalin, arbutin, salicin, melibiose, raffinose, starch, glycogen, xylitol, gentiobiose, D-lyxose D- and L-fucose, D- and L-arabitol and 2- and 5-ketogluconate.

The strain has been characterized by SDS gel electrophoresis, in which it has been compared to six other strains of *Lactobacillus paracasei* subsp. *paracasei*, vide the accompanying figure. In this comparison it has been shown to differ from all other described strains and at the same time as it when being compared to other lactobacilli appears to belong to the designated species. It has also been characterized with regard to ribosomic RNA in a so called Riboprinter®. With this method the strain has been shown to possess 76% similarity with the type strain for *Lactobacillus paracasei* subsp. *paracasei* and 72% similarity to the type strain of *Lactobacillus casei* analyzed at the same occasion.

The strain has been deposited at Belgian Coordinated Collections of Microorganisms—BCCM, LMG collection, and there been given the accession No. LMG P-17806.

The Advantages of the Strain

LMG P-17806 has, when compared to known strains of Lactobacillus, crucial advantages in the use as probiotics in food and naturopathic medicines, i.e., medical food, by a unique combination of good properties;

the strain has good resistance against gastric juice and bile salts, but unlike many other strains it does not deconjugate the bile salts;

it has a great ability to assimilate cholesterol;

the strain is well managing the passage through the stomach;

the strain has an influence on the conditions in the model of large intestine by increasing the production of L-lactic acid therein;

the strain is not more pro-inflammatory than common yogurt bacteria;

the strain prevents intestinal cells from being invaded by pathogenic microorganisms, such as Salmonella typhmurium;

the strain has an antagonistic action against the gastric ulcer bacterium Helicobacter pylori:

the strain forms bacteriocins which are active against clostridiae;

the strain survives well in milk as well as in frozen and dried form;

the strain, unlike most other lactobacilli has a favourable influence on the taste of fermented milk products (does not give any tang).

The present strain of *Lactobacillus paracasei* subsp. *paracasei* can be used as an additive to food or as naturopathic medicine, so called "Medical Food", or as an additive to naturopathic medicine.

Such medicines can be used for children with the purpose of alleviating atopic problems; for elderly persons in order to correct altered microflora caused by normal alterations by age or an altered secretion of hydrochloric acid; and for persons in general in order to normalize the intestine flora, whereas the content of clostridium bacteria is decreasing, lactobacilli and bufido bacteria being increased and high contents of coliformic bacteria being decreased.

By means of these properties the strain LMG P-17806 differs from previously known strains, which will be shown in the examples below.

Preparation of the Strain

The strain is prepared in the usual way for lactobacilli. A substrate suited for lactobacilli is used. This substrate should for instance contain at least one of the carbohydrates which the strain can ferment according to what is stated above, in combination with proteins, vitamins, minerals and other nutrients which normally are required by lactobacilli. Examples of suitable commercial substrates are yeast extract-glucose broth, MRS (de Man-Rogosa-Sharp broth), Rogosa, milk added with a minor amount of a yeast extract, etc. The strain is cultivated microaerophilicly or in the complete absence of oxygen, suitably at a temperature between +15° C. and +42° C. If the substrate is grafted with 0.1 to 1% of graft a culture time of between 10 and 40 hours is suitable. The strain can, if desired, be concentrated by centrifugation or filtration followed by washing the concentrate in order to remove the culture medium. The concentration can then be frozen or lyophilized in the common way. In this way preparations of between 100 millions and 100,000 millions of living bacteria LMG-P-17806 per g can be prepared. A preparation can then be used as such or be used as an additive to food, for instance to milk or another product which gives LMG P-17806 the possibility to survive and, if desired, to grow.

Investigations

A. Investigation Concerning the Passage of the Strain Through the Gastrointestinal Tract LMG- P-17806 was cultivated in the way described above and added together with yogurt culture to milk. A fermented product was produced by incubating the milk for five hours at +42° C. A palatable product was obtained which contained fully 100 millions living LMG P-17806 per gram of product. Healthy persons were given 3×200 g product daily for one week. The total intake of LMG P-17806 was between 40 billions and 200 billions.

Faeces samples were examined before the intake, after one week of consumption and one week after the intake had ceased. As is evident from Tables 1 and 2 below, a strong increase in the number of lactobacilli in the test subjects was obtained. Two isolates per test subject were classified as to species on each occasion, i.e. 20 isolates in total. 18 of the isolates for the consumption time appeared to consist of LMG P-17806 according to fenotypical classification. This bacteria strain was not discovered in the samples before or after the intake of LMG P-17806.

In average the contents of the faeces samples during the supply were very high and varied only moderately from 63 millions to 320 millions per gram, i.e. with a factor of 5. Noteworthy was, that the contents were largely the same independent of what contents were measured before the start of the experiment. After the supply had ceased the contents reverted to what seems to be natural for the test subject in question.

Tables 1 and 2 below the content of lactobacilli in faeces determined, in millions per gram, by plating and using the substrate Rogosa.

TABLE 1

5 test subjects with originally low content of *lactobacilli*

| Test subject | Before the experiment | During the experiment | After the experiment |
|---|---|---|---|
| 1 | 0.05 | 120 | 0.07 |
| 2 | 0.15 | 320 | 0.12 |
| 3 | 0.08 | 97 | 0.14 |
| 4 | 0.009 | 63 | 0.02 |
| 5 | <0.001 | 278 | 0.002 |

TABLE 2

5 test subjects with high contents of *lactobacilli*

| Test subject | Before the experiment | During the experiment | After the experiment |
|---|---|---|---|
| 6 | 1.2 | 297 | 1.3 |
| 7 | 0.7 | 83 | 0.6 |
| 8 | 0.2 | 136 | 0.18 |
| 9 | 4.3 | 74 | 3.5 |
| 10 | 0.6 | 212 | 0.8 |

The examination shows that the strain has good survival at the passage through the gastrointestinal tract.

B. Examination Concerning the Formation of L-lactic Acid by the Strain in a Model of Large Intestine The fermented product above was added to a so called SHIME-reactor which is an in vitro model of the intestine. Samples were taken from the part of the reactor which corresponds to the most important parts of the large intestine. Similar comparative tests were carried out with some other Lacto bacillus strains, i.a. closely related *L. paracasei* subsp. *paracasei*. As is evident from the following Table 3 below LMG P-17806 gave a strong increase in the production of L-lactic acid, which is the very lactic acid isomer which is generated by LMG P-17806. A production of lactic acid is considered as favourable for several reasons, i.a. considering the anti-bacterial effect of the lactic acid as well as the fact that a lower pH is supposed to reduce the availability and formation of nitrogen compounds.

TABLE 3

Production of L- and D-lactic acid in a SHIME-reactor after the addition of different lactic acid bacteria in mg per litre reactor content

| Lactic acid bacteria | Reactor 4 | | Reactor 5 | | Reactor 6 | |
|---|---|---|---|---|---|---|
| | L | D | L | D | L | D |
| LMG P-17306 | 300 | 80 | 500 | 100 | 280 | 90 |
| L. paracasei | 40 | 80 | 200 | 70 | 130 | 40 |
| L. rhamnosus | 90 | 10 | 10 | 70 | 80 | 10 |
| L. plantarum | 60 | 50 | 60 | 70 | 40 | 50 |

In the table "L" refers to the laevorotatory isomer of lactic acid and "D" to the dextrorotatory isomer.

Reactor 4 corresponds to the upper part of the large intestine, reactor 5 to the middle part and reactor 6 to the lower part of the large intestine. The investigation shows that the strain is forming L-lactic acid in the model of the large intestine.

C. Investigation of How the Strain is Protecting Intestinal Epithelium Cells from Invasion of *Salmonella Typhimurium*

Intestinal epithelium cells of the type CaCo-2 cells were cultivated in-vitro. These were added with a combination of lactobacilli and Salmonella typhimurium in the ratio 100:1 with the addition of 1 million salmonella per ml. The effect was studied after incubation for 120 min at 370° C. The amount of invading salmonella was determined by washing the plates with adhering CaCo-2 cells three times. The adhering cells were treated with the antibioticum gentamycin in a concentration of 100 mg/l for one hour in order to kill all bacteria which had not invaded cells. Then the plates were washed with PBS in order to remove all gentamycin and finally the entrapped bacteria were released by treating the CaCo-2 cells with 0.1% Triton-X during shaking. The number of salmonella was then determined by common plating methodology. LMG P-17806 had a pronounced effect in that it reduced a number of invaded cells. The closely related paracasei-variant 506 on the other hand seemed rather to stimulate the invasion of salmonella bacteria. Also with regard to this property LMG P-17806 showed a positive effect. The results are reported in Table 4 below.

TABLE 4

Invasion of salmonella

| | % invading salmonella | |
|---|---|---|
| Lactic acid bacteria | without lactic acid bacteria | with lactic acid bacteria |
| LNG P-17806 | 2.5 | 0.75 |
| L. paracaseiK 506 | 2.5 | 7 |
| L. plantarium | 2 | 2 |
| L. rhamnosus | 2.5 | 0.75 |

The table shows that the strain LMG P-17806 gives a marked protection against invasion of salmonella bacteria.

D. Investigation of Protection Against *Helicobacter Pylori*

In a mouse model where the mice had been infected with *Helicobacter pylori* the effect of supplying a fermented milk product with a strain of LMG P-17806 on one hand and without said strain on the other on the content of *H. pylori* measured in faeces was examined.

The mice were infected with 100 millions of the strain *H. Pylori* 17874 in helical form at three occasions with an interval of one day. Then the mice were given experimental products and the content of *H. pylori* in faeces was measured by means of heparinised magnetic balls and Enzyme Immuno Assay. Three products were examined. All the fermented milk products appeared to reduce the share of *H. pylori*, but the effect was occurring considerably faster in the cases when the product contained LMG P-17806 in comparison to common yoghurt and in comparison with a strain of *L. fermentum* KLD, respectively.

TABLE 5

Content of *H. pylori* in faeces measured by heparinised magnetic balls and Enzyme Immuno Assay

| Product | before intake | after intake for 2 days | after intake for 7 days | 7 days after cease of intake |
|---|---|---|---|---|
| Common yoghurt | 1.48 | 1.86 | 0.63 | 2.25 |
| Yoghurt with L. Fermentum | 1.65 | 1.62 | 0.94 | 1.61 |
| Yoghurt with LMG P-17806 | 1.80 | 0.68 | 0.61 | 1.71 |

The figures in the table state the absorbency of 405 nm and are relative contents.

E. Examination of the Influence of the Strain LMG P-17806 on the Immunological Defence The immunological defence system is controlled by a series of signal substances, so called cytokins. Some of these can be proinflammatory. The influence of LMG P-17806 on the production of cytokins TNF-alfa and IL-6 was compared with the influence of the two species contained in a yoghurt culture, *L. delbruckei* subsp. *bulgaricus* and *Streptococcus thermophilus*. Leucocytes were separated from human blood and added to living bacteria or bacteria killed with glutaraldehyde in an amount of 10 millions of leucocytes. As control lipopolysacharides (LPS) from *E. coli* were used. The results are reported in Table 6 below. The results show that the LMG P-17806 has the same inflammatory properties as a common yoghurt culture in the model used.

TABLE 6

The influence of the strain LMG P-17806 on the immunological defence

| Lactic acid bacteria | TNF-alpha mg/l | | IL-6 mg/l | |
|---|---|---|---|---|
| | living | killed | living | killed |
| S. thermophilus, E584 | 12 | 1 | 0.4 | <0.1 |
| L. bulgaricus, E535 | 2 | 3 | 0.5 | 0.1 |
| LMG P-17806 | 4 | 1 | 0.7 | <0.1 |

F. Examination of the Resistance of the Strain LMG P-17806 Against Antibiotics

Probiotics can be useful for use in connection with disorders in the balance of the intestine flora during medication with antibiotics. At the same time it is important that probiotics do not contribute to spreading of resistance to antibiotics, and this is especially important in the contemporary use of probiotics and antibiotics. The resistance of the strain LMG P-17806 against different antibiotics has been established for that reason. The sensitivity of the strain LMG P-17806 to different antibiotics were determined by establishing the content at which a reduction in the growth of the strain by 50%, measured as optical density, was obtained.

It appeared that the strain LMG P-17806 was resistant against vancomycin and was not inhibited even by 256 mg/l. The strain showed some resistance against trimethoprim and cefotaxime, an optical density (OD) of 50% at 12 and 4 mg/l, respectively being obtained. The strain LMG P-17806 was on the other hand sensitive to chloraphenicol, erythromcyin, rifampicin and tetracycline, where already levels below 1 mg/l resulted in an inhibition of the growth by 50%.

The influence by antibiotics was also examined as a survey by using so called Sensi discs from Oxoid. According to these results LMG P-17806 was resistant against aztreonam, ceftaximid, cefoxitin, colistine sulphate, kanamycin, polymyxin B, streptomycin and vancomycin.

LMG P-17806 might thus according to these results be especially interesting for use at the same time as therapy with antibiotics such as vancomycin, trimethoprim as well as several cefloxacins, which all are antibiotics with known side effects on the intestine flora and intestine function.

The Use of the Strain LMG P-17806

EXAMPLE 1

Preparation of Bacterial Concentrate

A frozen bacterial concentrate with 10 billions of LMG P-17806 per gram was prepared in the way stated above by cultivating the lactobacilli in a substrate of whey added with 1 g yeast extract per liter at a constant pH of 5.5 for 14 hours at 36° C. The bacteria were separated by centrifugation with continuous washing of the centrifugate. The concentrate was frozen in liquid nitrogen and then stored at −80° C. until use.

EXAMPLE 2

Preparation of Fermented Milk Product

A product milk was prepared from milk by homogenizing the milk, heat-treating it at +95° C. for five minutes and tempering it to +37° C. The product milk was grafted with 0.01% of a commercial, frozen yogurt culture and 0.5% of the LMG P-17806 concentrate. The cultures were allowed to grow for six hours at the temperature stated. The milk had then coagulated and the pH decreased to 4.55. The coagulated form was broken and the product chilled to +12° C. and then it was packed in common plastic cups, which are normally used for yogurt, and after-cooled in a refrigerating chamber having a temperature of +5° C. for one day and night. pH had then decreased to 4.4. The product was then stored at +8° C. for up to three weeks.

The content of the strain LMG P-17806 was monitored and as is seen from the results in Table 7 below, there was a limited growth of the strain LMG P-17806 during the culture and LMG P-17806 survived storing for three weeks at pH below 4.4 very well.

TABLE 7

The storability of the strain LMG P-17806 in milk product

| Graft | Content in product milk | Content after cultivation | After storing for 1 week | After storing for 2 weeks | After storing for 3 weeks |
|---|---|---|---|---|---|
| 9900 | 49 | 97 | 132 | 118 | 121 |

The contents are given in millions per gram.

The product had a normal appearance with a separation of whey of barely 1% after storing for fourteen days. The product tasted excellent and had uniform consistency and a fresh, mild flavor. The test product received better judgements than normal yogurt in an independent consumer survey carried out by an research institute. The product was compared in a consumer survey, in which the testing persons did not know what product was tasted, with a corresponding product without the strain LMG P-17806. The product with LMG P-17806 was preferred by 74% of the persons of the testing panel, and it received the average value of 7.6 in a scale of 9 points, which is significantly higher than the result for common yogurt. The judgement was slightly more than 1 point higher than previously known probiotic culture with *Lactobacillus acidophilus*. The results also differ from those previously obtained in comparison between pure yogurt and mixed products of yogurt and the probiotic bacteria *Lactobacillus acidophilus* and *Bifidobacterium longum*, respectively. No significant differences could be noted between pure yogurt and the respective mixed product in these comparisons.

EXAMPLE 3

Suitable Addition of the Strain LMG P-17806

Experiments were also carried out in order to find out the suitable range for the addition of the strain LMG P-17806. Milk was treated and then added with yogurt culture according to the above, whereas the addition of concentrate of the strain LMG P-17806 was varied from 5% to 0.01%. At such a high content as 5% graft of LMG P-17806 a tang was obtained, which probably originated from components of the graft itself. The change in pH was normal, however, and the appearance of the product was normal. The content of LMG P-17806 in fresh product was 504 millions per gram and the contents remained at this level during the storage. At the addition of 0.01% LMG P-17806 concentrate the product could not sensoricly be distinguished from common yogurt and the content of LMG P-17806 was already after one week less than one million per ml, which is the lowest content a product must contain in order to be allowed to state the product to contain a specific probiotic according to proposal to international regulation.

EXAMPLE 4

Preparation on Fermented Special Product

The experiment was carried out as above except that the milk also was added with 0.4 g yeast extract per liter. The graft was performed with 0.01% of the same yogurt culture as above, but only 0.1% LMG P-17806 concentrate was added. Incubation was carried out at +34° C. for 8 hours and then the product chilled, packed and stored as in Example 3 above. LMG P-17806 grew ten times under these conditions and similarly to the above the bacteria survived well during storage. The results are reported in the Table below.

TABLE 8

The storability of the specific milk product of the strain LMG P-17806

| Graft | Content in milk product | Content after cultivation | After storing for one week | After storing for two weeks | After storing for three weeks |
|---|---|---|---|---|---|
| 9900 | 10 | 103 | 114 | 109 | 107 |

The contents in the table are given in millions per gram product.

The product had a normal appearance with a separation of whey of 1.5% after storing for fourteen days. The product had a good, dry flavor and homogeneous consistency.

EXAMPLE 5

Preparation of Vegetable Juice Containing the Strain LMG P-17806

A vegetable juice was prepared by mixing carrot concentrate and an orange juice concentrate in equal parts so that pH of the finished mixture became pH 3.9. The mixed beverage was heat-treated and added with 1% and 0.1%, respectively, of LMG P-17806 concentrate. The content of LMG P-17806 became 100 and 10 millions per ml, respectively. The beverages were stored at +7° C. for four weeks. The flavor of the product was not affected and no influence by storing or addition of LMG P-17806 was observed. Addition of LMG P-17806 to a content exceeding 50 millions, however, seemed to reduce the decrease in vitamin C. In a product without LMG P-17806, like in the product having 10 millions bacteria per ml, the content of vitamin C decreased from 25 mg/100 g, before the storage to 18 mg/100 g after four weeks. With the addition of 100 millions LMG P-17806 ml the content of vitamin C only decreased to 22 mg/100 g, i.e., more than 50% lower decrease in the content of vitamin C. LMG P-17806 survived well and the content of LMG P-17806 after four weeks was only about 40% lower than in fresh product independent of the amount added.

In another experiment the same fruit beverage was added with 5% LMG P-17806. This gave a tang, which grew worse during storage time.

EXAMPLE 6

Preparation of Cereal Powder Based Food Product

Cereal powder based food product is manufactured in the common way. LMG P-17806 concentrate, according to the above is lyophilized after mixing with corn starch and stored after being packed in an oxygen-tight wrapping at a temperature of −20° C., The lyophilized preparation contained 61 billions LMG P-17806 per gram. The cereal was dried-mixed with 0.03% LMG P-17806 and packed in an atmosphere of nitrogen gas in an oxygen tight wrapping. The cereal was stored initially for three months at +12° C. and thereafter at a room temperature for additional four months. The content of LMG P-17806 is apparent from Table 9 below. The cereal gave good possibilities for survival to LMG P-17806 and therefore it is possible to prepare, for instance, baby food products having a high content of LMG P-17806.

TABLE 9

| Lyophilized preparation | Cereal before addition | Cereal after addition | After 3 months | After 7 months |
|---|---|---|---|---|
| 61,000 | <0.0001 | 20 | 18 | 6.5 |

The content in the Table 9 are given in millions per gram cereal.

The cereal was dissolved in 9 parts of water of +50° C. and the content of LMG P-17806 determined. The content was 1 million LMG P-17806 per ml beverage in the case that the cereal was formulated as a six months' old food product. The cereal could not be distinguished from common product. After storing for one night in room temperature, however, the cereal added with LMG P-17806 tasted slightly acid and had pH of 5.7.

In a second experiment the effect of the addition of 1% and 0.001%, respectively, of lyophilized LMG P-17806 preparation was examined. The contents thereof in the cereal after the addition were 570 and 0.8 millions per gram respectively.

The cereals were stored in a corresponding way and examined after storage for 5 months. After dissolution as above the content in the prepared cereal was 800 millions, respectively for the low addition less than 10,000 per ml. With the high addition a slightly acid flavor was noted already after storing for four hours of the cereal at body temperature.

EXAMPLE 7

Preparation of Dried Power for Use as "Medical Food"

A lyophilized LMG P-17806 concentrate was mixed with different amounts of corn starch in the proportions in 1:1, 1:9, 1:99 and 1:999, respectively. The mixed powders were stored in small sachets with 1 to 100 g per sachet. The material of the sachets was impervious to oxygen and water vapor. The sachets were stored in freezer, refrigerator and room temperature, respectively. The content was then used as an additive to beverage by mixing the powder with the beverage before the beverage being consumed. The corresponding survival as in example 6 above was obtained. The powder with the proportions 1:1 was also packed in gelatin capsules with 0.4 g per capsule. The number of bacteria per capsule was 10 billions. The capsules were blister-packed in a material with good barrier properties against oxygen and water vapor. The capsules were stored in the same way as stated above and corresponding good survival results were obtained.

EXAMPLE 8

Preparation and Use of Bacterial Mixes

LMG P-17806 can be mixed with other lactobacilli without inhibiting them. LMG-17806 does not seem to form any substances which are inhibiting other lactobacilli or lactococci where LMG P-17806 are co-cultivated with yogurt cultures, sour milk cultures with lactococci or other lactobacilli species such as *L. acidophilus, L. fermentum* or *L. rhamnosus*. Experiments with mixtures of lyophilized preparations containing all these bacteria have indicated unchanged storage properties whether mixing was carried out with corn starch or with pap powder. After the solution of the pap powder and a storage for 12 hours at body temperature and 12 hours at room temperature no negative influence by LMG P-17806 could be traced either on the total content of lactobacilli or on the content of either of the bacteria.

In an experiment to produce probiotic sour milk 0.5% of sour milk culture and 0.6% of lyophilized concentrate of each of *L. acidophilus* NCFB 1748, *L. fermentum* KLD and LMG p-17806 were added to normal treated product milk. However, only 0.1% KLD was added, because higher additions gave rise to tang and to a bad coagulum. Milk was stored for 19 hours at room temperature. Then the pH thereof was 4.50. The milk was cooled to +10° C., packed and stored at +6° C. or up to 14 days. The results are evident from the following table 10.

TABLE 10

| Lactic acid bacteria | Before cooling | After 5 days | After 14 days |
| --- | --- | --- | --- |
| Lactococci | 730 | 810 | 580 |
| L. acidophilus | 135 | 142 | 131 |
| L. fermentum | 12 | 14 | 9 |
| LMG P-17806 | 112 | 126 | 109 |

The contents are in millions per ml of the different bacteria.

80 healthy test subjects were given the products to eat in connection with a conference journey to Istanbul in Turkey. The group was divided into two, one eating a sour milk according to the above with only LMG P-17806 whereas the other ate the probiotic sour milk with three different probiotic strains. The test subjects were on the conference place for 8 days. They started to eat the products two days before departure to the conference place and continued to eat for four days after home-coming. The products were eaten as 3 snacks evenly spread during the day with 150 g/meal. All test subjects except 2 persons of the sour milk group declared that they ate the product according to the scheme. In an inquiry they were asked to state discomforts from the gastrointestinal tract in the form of stomach pains, tensions, diarrhoea or constipation on a scale of 3 degrees. Apart from diarrhoea there was a difference so far that 5% of the test subjects which only had eaten LMG P-17806 stated that they had had serious or very serious diarrhoea during at least two days whereas this frequency only was 22% in the group which ate the probiotic sour milk.

Thus it seems as if a mix of several different lactobacilli might be still more effective than only one single strain of bacteria. This can be due to the fact that the lactobacilli administered had different properties.

What is claimed is:

1. An isolated strain of *Lactobacillus paracasei* subsp. *paracasei*, LMG-P-17806, said strain being a Gram-positive, homofermentative, rod-shaped bacterium capable of producing L-lactic acid and containing three plasmids having a size of 2.2, 4.36 and 9.1 Kb, respectively.

2. The strain according to claim 1, wherein the strain contains 44% GC.

3. The strain according to claim 1, wherein the strain has been isolated from samples from the gastrointestinal microflora of humans.

4. The strain according to claim 1, wherein the strain can ferment ribose, adonitol, galactose, glucose, fructose, mannose, sorbose, mannitol, sorbitol, N-acetyl-glucosamine, esculin, cellobiose, maltose, lactose, sucrose, trehalose, inulin, melezitose, D-turanose and D-tagatose.

5. The strain according to claim 1, wherein the strain is provided as a concentrate in the form of a frozen or lyophilized powder.

6. A method for producing food products, said method comprising:
  adding *Lactobacillus paracasei* subsp. *paracasei*, LMG P-17806 to a food product selected from the group consisting of a milk product, a fermented milk product, a powdered cereal based food, a food for infants, a food for small children, a fruit beverage and a vegetable beverage, in an amount of between 0.001% and 5% of the food product.

7. The method of claim 6 wherein the strain is present in an amount of between 1 million and 10 billion living bacteria per gram of the product.

8. The method of claim 6, wherein the strain is added in a content of between 0.01% and 1%.

9. A method for cultivating the strain of *Lactobacillus paracasei* subsp. *paracasei,* LMG P-17806, said method comprising:
   growing the strain together with other lactic acid bacteria used in the production of fermented food products.

10. The method of claim 7 wherein the strain is present in an amount of between 1 million and 10 billion living bacteria per gram of the food.

11. A composition containing the strain *Lactobacillus paracasei* subsp. *paracasei,* LMG P-17806, said composition comprising:
   a food product selected from the group consisting of a milk product, a fermented milk product, a vegetable beverage, a fruit beverage, a powdered cereal based product, a food for infants, and a food for small children, said food product containing the strain *Lactobacillus paracasei* subsp. *paracasei* in an amount of $5 \times 10^5 – 5 \times 10^9$ living bacteria, corresponding to 0.0005–0.5% of the food product.

12. The composition according to claim 11 wherein the food product further comprises a yeast extract or a nutrient which contributes to growth or survival of *Lactobacillus paracasei* subsp. *paracasei* in the food product.

13. The product of claim 12, wherein the yeast extract is present in an amount between 0.01 and 0.1%.

14. The product according to claim 12, wherein the strain is in the form of a concentrate in a frozen or a lyophilized condition for mixing in direct connection with consumption occasion into the food product.

15. The composition according to claim 11, wherein the strain is present in the form of a concentrate in a frozen or a lyophilized condition for mixing at the time of consumption of the food product.

16. The product of claim 11 wherein the strain is in an amount of $1 \times 10^5 – 10^9$ living bacteria.

17. A food product comprising:
   a beverage selected from the group consisting of a milk product, a fermented milk product, a fruit beverage and a vegetable beverage; and
   the strain of *Lactobacillus paracasei* subsp. *paracasei,* LMG P-17806 present in said beverage in an amount of between 0.001% and 5%.

18. The food product of claim 17, wherein the strain is present in an amount of between 0.01% and 1%.

19. The food product of claim 18 wherein the strain is present in an amount of between 1 million and 10 billion living bacteria per gram of the food.

20. The food product of claim 17 wherein the strain is present in an amount of between 1 million and 10 billion living bacteria per gram of the food.

21. A composition containing the strain *Lactobacillus paracasei* subsp. *paracasei,* LMG P-17806, said composition comprising:
   a concentrated nutritional supplement wherein the strain *Lactobacillus paracasei* subsp. *paracasei* is present at a content of 1–100 billion living bacteria corresponding to 0.001–100% of the concentrated nutritional supplement.

22. The composition according to claim 21 wherein the nutritional supplement further comprises a nutrient for enhancing survival of the bacteria.

23. The composition according to claim 22, wherein the strain is in the form of a concentrate in a frozen or a lyophilized condition for mixing in direct connection with consumption occasion into the nutritional supplement.

24. The composition according to claim 21, wherein the strain is present in the form of a concentrate in a frozen or a lyophilized condition for mixing at the time of consumption of the nutritional supplement.

\* \* \* \* \*

UNITED STATES PATENT AND TRADEMARK OFFICE
CERTIFICATE OF CORRECTION

PATENT NO. : 6,599,504 B1
DATED : July 29, 2003
INVENTOR(S) : Wadstrom et al.

It is certified that error appears in the above-identified patent and that said Letters Patent is hereby corrected as shown below:

<u>Title page,</u>
Item [73], Assignee, should read as follows: -- [73] Assignee: Arla Foods AB, Stockholm (SE) --

Signed and Sealed this

Seventeenth Day of February, 2004

JON W. DUDAS
*Acting Director of the United States Patent and Trademark Office*